US012099063B2

United States Patent
Wei

(10) Patent No.: US 12,099,063 B2
(45) Date of Patent: Sep. 24, 2024

(54) COMPOSITIONS, KITS, AND METHODS FOR MULTIPLEX ASSAYS TO CORRECT FOR BIOTIN INTERFERENCE IN TARGET ANALYTE MEASUREMENTS

(71) Applicant: Siemens Healthcare Diagnostics Inc., Tarrytown, NY (US)

(72) Inventor: Tie Wei, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 282 days.

(21) Appl. No.: 17/650,579

(22) Filed: Feb. 10, 2022

(65) Prior Publication Data

US 2022/0163533 A1 May 26, 2022

Related U.S. Application Data

(62) Division of application No. 17/250,675, filed as application No. PCT/US2019/051895 on Sep. 19, 2019, now Pat. No. 11,287,429.

(60) Provisional application No. 62/735,905, filed on Sep. 25, 2018.

(51) Int. Cl.
*G01N 33/542* (2006.01)
*B01L 3/00* (2006.01)
*G01N 21/76* (2006.01)
*G01N 33/58* (2006.01)

(52) U.S. Cl.
CPC ...... *G01N 33/582* (2013.01); *B01L 3/502715* (2013.01); *G01N 21/76* (2013.01); *G01N 33/542* (2013.01)

(58) Field of Classification Search
CPC ..... G01N 33/542; G01N 33/582; G01N 21/76
See application file for complete search history.

(56) References Cited

U.S. PATENT DOCUMENTS

| 5,212,063 | A | 5/1993 | Ofenloch-Hahnle et al. |
| 5,340,716 | A | 8/1994 | Ullman et al. |
| 2005/0147531 | A1 | 7/2005 | Buechler |
| 2010/0034445 | A1 | 2/2010 | Ulmer |
| 2011/0009293 | A1 | 1/2011 | Akhawan-Tafti |
| 2015/0072438 | A1 | 3/2015 | Teng et al. |
| 2015/0198528 | A1 | 7/2015 | Manneh |

(Continued)

FOREIGN PATENT DOCUMENTS

| CN | 103837675 | 6/2014 |
| CN | 106662532 | 5/2017 |
| IN | 102348980 | 2/2012 |

(Continued)

OTHER PUBLICATIONS

International Search Report for PCT/US2019/051895 dated Dec. 3, 2019.

(Continued)

*Primary Examiner* — Gailene Gabel

(57) ABSTRACT

Kits containing a multiplexed chemiluminescent detection system and microfluidics devices and methods for detecting the presence and/or concentration of biotin and at least one target analyte in a sample are disclosed. The kits, microfluidics devices, and methods utilize singlet oxygen-activatable chemiluminescent compounds in combination with two or more fluorescent molecules that emit light at different wavelengths.

14 Claims, 9 Drawing Sheets

(56) References Cited

U.S. PATENT DOCUMENTS

2020/0003445 A1    1/2020   Oberhaensli
2021/0247398 A1*   8/2021   Wei ..................... G01N 33/542

FOREIGN PATENT DOCUMENTS

WO    2014152322    9/2014
WO    2015148479    10/2015

OTHER PUBLICATIONS

Rodriguez et al., Biotin at High Concentrations interferes with the LOCI Digoxin Assay but the PETINIA Phenytoin Assay Is Not Affected., Annals of Clinical & Laboratory Science, 48(2), 164-167 (Mar. 2018).

* cited by examiner

Assay Components

CB2 = chemibead with analyte-specific binding partner bound thereto

Biotinylated analyte specific binding partner

SB = sensibead with biotin-specific binding partner bound thereto

CB1 = chemibead with biotin/biotin analog bound thereto

Complexes formed when neither biotin nor target analyte is present in the sample Complexes formed when biotin and target analyte are present in the sample ◇ - biotin
● - target analyte

How Sample Biotin Interferes With Prx Signal In This Duplex Assay

Hypothetical Scenario: Prx Signal In The Absence And Presence Of Varying Amount Of S Biotin

| [PrX] ng/mL / [biotin] ng/mL | 0 | 10 | 100 | 500 | 3000 |
|---|---|---|---|---|---|
| 0 | 2 | 2 | 2 | 1 | 1 |
| 5 | 10 | 10 | 9 | 6 | 3 |
| 20 | 40 | 40 | 37 | 25 | 16 |
| 100 | 100 | 100 | 93 | 66 | 47 |
| 500 | 300 | 300 | 280 | 209 | 156 |

% Interference by S biotin on PrX signal

| [PrX] ng/mL / [biotin] ng/mL | 0 | 10 | 100 | 500 | 3000 |
|---|---|---|---|---|---|
| 0 | 2 | 0% | -10% | -46% | -73% |
| 5 | 10 | 0% | -9% | -41% | -66% |
| 20 | 40 | 0% | -8% | -37% | -59% |
| 100 | 100 | 0% | -7% | -34% | -53% |
| 500 | 300 | 0% | -7% | -30% | -48% |

FIG. 7

One Method of Correcting Target Analyte Signal Using Sample Biotin Signal (Or Concentration):

| [PrX] ng/mL / [biotin] ng/mL | 0 | 10 | 100 | 500 | 3000 |
|---|---|---|---|---|---|
| 0 | 2 | 2 | 2 | 1 | 1 |
| 5 | 10 | 10 | 9 | 6 | 3 |
| 20 | 40 | 40 | 37 | 25 | 16 |
| 100 | 100 | 100 | 93 | 66 | 47 |
| 500 | 300 | 300 | 280 | 209 | 156 |

The Shaded Rectangle Above Can Be Rearranged As Follows:

| PrX | Biotin | PrX signal |
|---|---|---|
| 5 | 0 | 10 |
| 20 | 0 | 40 |
| 5 | 100 | 9 |
| 20 | 100 | 37 |
| 5 | 500 | 6 |
| 20 | 500 | 25 |

Regression Is Conducted To Get The Correction Equation Based On The Data Above (This Can Be Done With Statistical Software):

Regression Equation

PrX = -1.62 + 0.5668 PrX signal + 0.01073 Biotin

FIG. 8

How To Correct Target Analyte Signal Using Sample Biotin Signal (Or Concentration):

| PrX | Biotin | PrX S |
|-----|--------|-------|
| 0   | 0      | 2     |
| 5   | 0      | 10    |
| 20  | 0      | 40    |
| 100 | 0      | 100   |
| 500 | 0      | 300   |
| 0   | 10     | 2     |
| 5   | 10     | 10    |
| 20  | 10     | 40    |
| 100 | 10     | 100   |
| 500 | 10     | 300   |
| 0   | 100    | 9     |
| 5   | 100    | 37    |
| 20  | 100    | 93    |
| 100 | 100    | 280   |
| 500 | 100    | 1     |
| 0   | 500    | 6     |
| 5   | 500    | 25    |
| 20  | 500    | 66    |
| 100 | 500    | 209   |
| 500 | 500    | 1     |
| 0   | 3000   | 3     |
| 5   | 3000   | 16    |
| 20  | 3000   | 47    |
| 100 | 3000   | 156   |
| 500 | 3000   |       |

Regression Analysis: PrX versus Biotin, PrX S

Analysis of Variance

| Source     | DF | Adj SS | Adj MS | F-Value | P-Value |
|------------|----|--------|--------|---------|---------|
| Regression | 2  | 840759 | 420380 | 143.87  | 0.000   |
| Biotin     | 1  | 24361  | 24361  | 8.28    | 0.009   |
| PrX S      | 1  | 840759 | 840759 | 287.74  | 0.000   |
| Error      | 22 | 64741  | 2943   |         |         |
| Total      | 24 | 913500 |        |         |         |

Model Summary

| S       | R-sq   | R-sq(adj) | R-sq(pred) |
|---------|--------|-----------|------------|
| 54.2472 | 92.90% | 92.25%    | 89.39%     |

Coefficients

| Term     | Coef    | SE Coef | T-Value | P-Value | VIF  |
|----------|---------|---------|---------|---------|------|
| Constant | -39.3   | 16.1    | -2.45   | 0.023   |      |
| Biotin   | 0.02746 | 0.00954 | 2.88    | 0.009   | 1.03 |
| PrX S    | 1.947   | 0.115   | 16.96   | 0.000   | 1.03 |

Regression Equation

PrX = −39.3 + 0.02746 Biotin + 1.947 PrX S

Fits and Diagnostics for Unusual Observations

| Obs | PrX   | Fit   | Resid | Std Resid |   |
|-----|-------|-------|-------|-----------|---|
| 20  | 500.0 | 383.1 | 117.9 | 2.32      | R |
| 25  | 500.0 | 347.3 | 152.7 | 3.26      | R |

R Large residual

Equation for Target Analyte (PrX) Correction. Here, PrX can be PrX signal at 0 ng/mL biotin. PrX column can be replaced by PrX S at 0 ng/mL biotin (where the PrX S values are 2, 10, 40, 100, and 300). In that case, the PrX signal is corrected before it is converted to analyte.

FIG. 9

COMPOSITIONS, KITS, AND METHODS FOR MULTIPLEX ASSAYS TO CORRECT FOR BIOTIN INTERFERENCE IN TARGET ANALYTE MEASUREMENTS

CROSS REFERENCE TO RELATED APPLICATIONS/INCORPORATION BY REFERENCE STATEMENT

The subject application claims benefit under 35 USC § 119(e) of U.S. provisional Application No. 62/735,905, filed Sep. 25, 2018. The entire contents of the above-referenced patent application are hereby expressly incorporated herein by reference.

STATEMENT REGARDING FEDERALLY SPONSORED RESEARCH OR DEVELOPMENT

Not Applicable.

BACKGROUND

Diagnostic assay reagents often include conjugates of antibodies or other small drug molecules with haptens, such as biotin and fluorescein. The tight binding of these haptens to large protein molecules (e.g., avidin/streptavidin for biotin and anti-FITC for fluorescein) that are coated on a solid support or surface provides a convenient way to immobilize the hapten-antibody or hapten-drug conjugate on the solid support/surface.

Biotin is well known in the art for its use as a food supplement; for example, biotin is utilized to promote healthy hair and nail growth and to treat various disease conditions. Given this use, significant biotin levels can be found in biological samples, such as (but not limited to) blood. Since biotin is used in many diagnostic assays (for example, to coat solid supports), high levels of biotin in test samples can interfere with assay signals in any assays where biotinylated assay components are employed. This is particularly true for assays such as those found on the Siemens' ADVIA CENTAUR® immunoassay system, DIMENSION EXL™ integrated chemistry system, and DIMENSION VISTA® LOCI® system (Siemens Healthcare Diagnostics Inc., Tarrytown, N.Y.), where biotinylated assay components are expected to bind streptavidin-coated solid supports.

Because interference is observed in various assay methods at different biotin concentrations, the levels of biotin present in patient samples should be quantitated to determine if the samples are suitable for use in particular assays. However, most currently available biotin assays have narrow ranges (i.e., 0-50 ng/ml) that are not suitable for detecting the wide dynamic range of biotin concentrations that are typically found in actual patient samples (i.e., 0-1500 ng/ml).

Using biotin as an example, there are three ways to mitigate the problem of hapten interference. One is using preformed reagent, i.e., a biotinylated assay component is "pre-bound" with the streptavidin-coated solid support during reagent production. Because of the tight binding and slow off-rate between streptavidin and biotin, replacing the already bound biotin from streptavidin by the incoming biotin in a patient sample is not a predominate process. The second way is to increase the streptavidin binding sites on the solid support, so that there are extra binding sites available for the sample biotin molecules in addition to the biotinylated assay components. The third way is the combination of both of the above. However, none of these three strategies truly solves the problem of biotin interference unless the use of biotin-streptavidin as active assay components is completely avoided. Another major issue with all of the above solutions is that assay components are involved in the prevention of interference, and this can easily affect the magnitude of the assay signal itself.

U.S. Pat. No. 5,212,063 teaches the use of polymer particles with a biotin binding core and a covering layer of protein, carbohydrate, or co-polymer for the purpose of filtering free biotin, but does not filter biotin conjugated to large molecules. This approach may be effective for some assay formats, but it also introduces particles that may generate extra absorbance that could interfere with assay signals.

The field of medical diagnostics utilizes many different forms of assay technologies. One example of a commercially used assay is the Luminescent Oxygen Channeling Assay (LOCI®) technology. The LOCI® advanced chemiluminescence assay is described, for example, in U.S. Pat. No. 5,340,716 (Ullman et al.), the entire contents of which are expressly incorporated herein by reference. The currently available LOCI® technology has high sensitivity and uses several reagents. In particular, the LOCI® assay requires that two of these reagents (referred to as a "sensibead" and a "chemibead") be held by other specific binding partner assay reagents in a manner whereby the sensibead and chemibead are in close proximity to one another to achieve a signal. Upon exposure to light at a certain wavelength, the sensibead releases singlet oxygen, and if the two beads are in close proximity, the singlet oxygen is transferred to the chemibead; this causes a chemical reaction that results in the chemibead giving off light that can be measured at a different wavelength.

However, there are no biotin assays available in the LOCI® format, or any currently available methods that eliminate interference caused by sample biotin in the LOCI® format.

Therefore, there is a need in the art for new and improved assays for detecting and correcting for biotin interference that overcome the disadvantages and defects of the prior art. It is to such assays, as well as kits and microfluidics devices containing same and methods of using same, that the present disclosure is directed.

BRIEF DESCRIPTION OF THE DRAWINGS

FIG. 7 contains a table providing a hypothetical scenario of data obtained by the multiplex assay according to the present disclosure and demonstrating the percent interference by sample biotin on target analyte signal.

FIG. 8 contains one non-limiting method by which target analyte signal can be corrected based upon sample biotin signal or concentration.

FIG. 9 contains another non-limiting method by which target analyte signal can be corrected based upon sample biotin signal or concentration.

DETAILED DESCRIPTION

Figure 1:
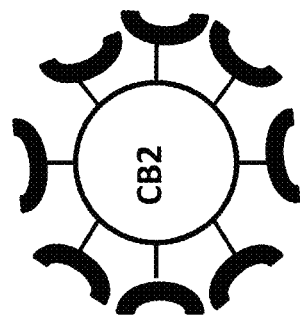
FIG. 1 schematically depicts multiplex assay components utilized in one non-limiting embodiment of the present disclosure.
Figure 1:
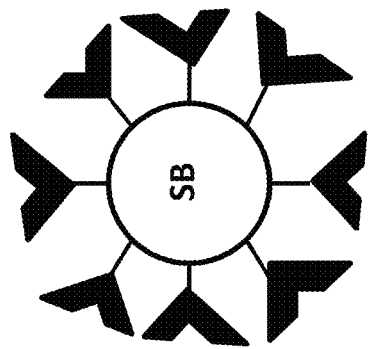
Figure 1:
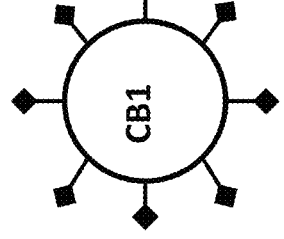

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutes and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/ device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

The terms "analog" and "derivative" are used herein interchangeably and refer to a substance which comprises the same basic carbon skeleton and carbon functionality in its structure as a given compound, but can also contain one or more substitutions thereto. The term "substitution" as used herein will be understood to refer to the replacement of at least one substituent on a compound with a residue R. In certain non-limiting embodiments, R may include H, hydroxyl, thiol, a halogenid selected from fluoride, chloride, bromide, or iodide, a C1-C4 compound selected one of the following: linear, branched or cyclic alkyl, optionally substituted, and linear branched or cyclic alkenyl, wherein the optional substitutents are selected from one or more alkenylalkyl, alkynylalkyl, cycloalkyl, cycloalkenylalkyl, arylalkyl, heteroarylalkyl, heterocyclealkyl, optionally substituted heterocycloalkenylalkyl, arylcycloalkyl, and arylheterocyclealkyl, each of which is optionally substituted wherein the optional substitutents are selected from one or more of alkenylalkyl, alkynylalkyl, cycloalkyl, cyclakenylalkyl, arylalkyl, alkylaryl, heteroarylalkyl, heterocyclealkyl, optionally substituted heterocycloalkenylalkyl, arylcycloalkyl, and a rylheterocyclalkyl, phenyl, cyano, hydroxyl, alkyl, aryl, cycloalkyl, cyano, alkoxy, alkylthio, amino, —NH (alkyl), —NH(cycloalkyl)$_2$, carboxy, and —C(O))-alkyl.

The term "sample" as used herein will be understood to include any type of biological sample that may be utilized in accordance with the present disclosure. Examples of fluidic biological samples that may be utilized include, but are not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

The term "specific binding partner," as used in particular (but not by way of limitation) herein in the terms "biotin-specific binding partner" or "target analyte-specific binding partner," will be understood to refer to any molecule capable of specifically associating with biotin or the target analyte, respectively. For example but not by way of limitation, the binding partner may be an antibody, a receptor, a ligand, aptamers, molecular imprinted polymers (i.e., inorganic matrices), combinations or derivatives thereof, as well as any other molecules capable of specific binding to biotin or the target analyte, respectively.

The term "antibody" is used herein in the broadest sense and refers to, for example, intact monoclonal antibodies and polyclonal antibodies, multi-specific antibodies (e.g., bispecific antibodies), antibody fragments and conjugates thereof that exhibit the desired biological activity of analyte binding (such as, but not limited to, Fab, Fab', F(ab')2, Fv, scFv, Fd, diabodies, single-chain antibodies, and other antibody fragments and conjugates thereof that retain at least a portion of the variable region of an intact antibody), antibody substitute proteins or peptides (i.e., engineered binding proteins/peptides), and combinations or derivatives thereof. The antibody can be of any type or class (e.g., IgG, IgE, IgM, IgD, and IgA) or sub-class (e.g., IgG1, IgG2, IgG3, IgG4, IgA1, and IgA2).

The term "hapten" as used herein refers to a small proteinaceous or non-protein antigenic determinant (or "epitope") which is capable of being recognized by a target analyte-specific binding partner, such as (but not limited to) an antibody. The term "polyhapten" as used herein will be understood to refer to a synthetic molecule that contains multiple epitopes/antigenic determinants attached thereto.

An "analyte" is a macromolecule that is capable of being recognized by an analyte-specific binding partner, such as (but not limited to) an antibody. Both analytes and haptens comprise at least one antigenic determinant or "epitope," which is the region of the antigen or hapten which binds to the analyte-specific binding partner (i.e., antibody). Typically, the epitope on a hapten is the entire molecule.

Certain non-limiting embodiments of the present disclosure are directed to multiplex assays for the detection of both biotin and target analyte(s) in samples as well as kits containing same and methods of use thereof. In some assay embodiments, signal producing system (sps) members comprise a sensitizer such as, for example, a photosensitizer, and two or more chemiluminescent-fluorescent molecule compositions (wherein a first chemiluminescent composition generates a signal related to the presence of biotin, whereas at least a second chemiluminescent composition generates a signal related to the presence of a target analyte); in these assay embodiments, activation of the sensitizer results in a product that activates the chemiluminescent composition(s), thereby generating a detectable signal that relates to the amount of bound target analyte and bound biotin being detected. An exemplary (but non-limiting) embodiment of an assay platform on which the present disclosure can be based is the Luminescence Oxygen Channeling Assay (LOCI®; Siemens Healthcare Diagnostics Inc., Tarrytown, N.Y.). The LOCI® assay is described, for example, in U.S. Pat. No. 5,340,716 (Ullman et al.), the entire contents of which are expressly incorporated herein by reference.

Any target analytes capable of detection via the assay formats described or otherwise contemplated herein may be detected by the multiplex assays of the present disclosure. Non-limiting examples of target analytes include: Procalcitonin (PCT), BNP, NT-proBNP, D-Dimer, CKMB, Myoglobin, Myeloperoxidase, ST2, hCG, LH, FSH, iPTH, TSH, $fT_4$, $T_4$, PSA, fPSA, and cPSA, and combinations thereof.

Certain non-limiting embodiments of the present disclosure are directed to a kit for performing multiplex assays that utilize a chemiluminescent detection system for determining the concentration of biotin and at least one additional target analyte in a sample. The kit includes: (a) a composition comprising a singlet oxygen-activatable chemiluminescent compound having biotin or an analog thereof directly or indirectly bound thereto, as well as a fluorescent molecule that is excited by the activated chemiluminescent compound; (b) a composition comprising a singlet oxygen-activatable chemiluminescent compound having a first analyte-specific binding partner for a target analyte directly or indirectly bound thereto, as well as a fluorescent molecule that is excited by the activated chemiluminescent compound, wherein the fluorescent molecule is different from the fluorescent molecule of (a) and emits light at a different wavelength than the fluorescent molecule of (a); (c) a biotinylated second analyte-specific binding partner for the target analyte, wherein the second analyte-specific binding partner binds to a different epitope of the target analyte than the first analyte-specific binding partner of (b); and (d) a composition comprising a sensitizer capable of generating singlet oxygen in its excited state and having a biotin-specific binding partner directly or indirectly bound thereto.

In certain non-limiting embodiments, the kit further includes (e) a composition comprising a singlet oxygen-activatable chemiluminescent compound having a first analyte-specific binding partner for a second target analyte directly or indirectly bound thereto, as well as a fluorescent molecule that is excited by the activated chemiluminescent compound, wherein the fluorescent molecule is different from the fluorescent molecules of (a) and (b) and emits light at a different wavelength than the fluorescent molecules of (a) and (b); and (f) a biotinylated second analyte-specific binding partner for the second target analyte, wherein the second analyte-specific binding partner binds to a different epitope of the second target analyte than the first analyte-specific binding partner.

A chemiluminescent compound (chemiluminescer) is a compound that is chemically activatable and, as a result of such activation, emits light at a certain wavelength. Examples of chemiluminescers, by way of illustration and not limitation, include: olefins capable of reacting with singlet oxygen or a peroxide to form hydroperoxides or dioxetanes, which can decompose to ketones or carboxylic acid derivatives; stable dioxetanes which can decompose by the action of light; acetylenes which can react with singlet oxygen to form diketones; hydrazones or hydrazides that can form azo compounds or azo carbonyls such as (but not limited to) luminol; and aromatic compounds that can form endoperoxides, for example. As a consequence of the activation reaction, the chemiluminescers directly or indirectly cause the emission of light.

In certain embodiments, the singlet oxygen-activatable chemiluminescent compound may be a substance that undergoes a chemical reaction with singlet oxygen to form a metastabile intermediate species that can decompose with the simultaneous or subsequent emission of light. The composition comprising the chemiluminescent compound may be directly excited by the activated chemiluminescent compound; alternatively, the composition may further comprise at least one fluorescent molecule that is excited by the activated chemiluminescent compound.

A sensitizer is a molecule, usually a compound, that generates a reactive intermediate such as, for example, singlet oxygen, for activation of a chemiluminescent compound. In some non-limiting embodiments, the sensitizer is a photosensitizer. Other sensitizers that can be chemi-activated (by, e.g., enzymes and metal salts) include, by way of example and not limitation, other substances and compositions that can produce singlet oxygen with or without activation by an external light source. For example, certain compounds have been shown to catalyze the conversion of hydrogen peroxide to singlet oxygen and water. Non-limiting examples of other sensitizer substances and compositions include: oxides of the alkaline earth metals Ca, Sr, and Ba; derivatives of elements of groups 3A, 4A, 5A, and 6A in $d^0$ configuration; oxides of actinides and lanthanides; and oxidizers $ClO^-$, $BrO^-$, $Au^{3+}$, $IO_3^-$, and $IO_4^-$; and in particular, molybdate, peroxomolybdate, tungstate, and peroxotungstate ions, and acetonitrile. The following references, which are hereby expressly incorporated by reference in their entirety, provide further disclosure regarding sensitizer substances and compositions that also fall within the scope of the present disclosure: Aubry, *J. Am. Chem. Soc.*, 107: 5844-5849 (1985); Aubry, *J. Org. Chem.*, 54:726-728 (1989); Böhme and Brauer, *Inorg. Chem.*, 31:3468-3471 (1992); Niu and Foote, *Inorg. Chem.*, 31:3472-3476 (1992); Nardello et al., *Inorg. Chem.*, 34:4950-4957 (1995); Aubry and Bouttemy, *J. Am. Chem. Soc.*, 119:5286-5294 (1997); and Almeida et al., *Anal. Chim. Acta*, 482:99-104 (2003); the entire contents of each of which are hereby expressly incorporated herein by reference.

Also included within the scope of photosensitizers are compounds that are not true sensitizers but which on excitation by heat, light, ionizing radiation, or chemical activation will release a molecule of singlet oxygen. Members of this class of compounds include, for example (but not by way of limitation), the endoperoxides such as 1,4-biscarboxyethyl-1,4-naphthalene endoperoxide; 9,10-diphenylanthracene-9,10-endoperoxide; and 5,6,11,12-tetraphenyl naphthalene 5,12-endoperoxide. Heating or direct absorption of light by these compounds releases singlet oxygen.

A photosensitizer is a sensitizer for activation of a photoactive compound, for example, by generation of singlet oxygen by excitation with light. The photosensitizers are photoactivatable and include, e.g., dyes and aromatic compounds, and are usually compounds comprised of covalently bonded atoms, usually with multiple conjugated double or triple bonds. The compounds should absorb light in the wavelength range of from about 200 nm to about 1,100 nm, such as (but not limited to) a range of from about 300 nm to about 1,000 nm or a range of from about 450 nm to 950 nm, with an extinction coefficient at its absorbance maximum greater than 500 $M^{-1} cm^{-1}$, or greater than 5,000 $M^{-1} cm^{-1}$, or greater than 50,000 $M^{-1} cm^{-1}$, at the excitation wavelength. Photosensitizers should be relatively photostable and may not react efficiently with singlet oxygen. Examples of photosensitizers, by way of illustration and not limitation, include: acetone; benzophenone; 9-thioxanthone; eosin;

9,10-dibromoanthracene; methylene blue; metallo-porphyrins such as (but not limited to) hematoporphyrin; phthalocyanines; chlorophylls; rose bengal; and buckminsterfullerene; as well as derivatives of these compounds.

Particular, non-limiting examples of chemiluminescent compounds and photosensitizers that may be utilized in accordance with the present disclosure are set forth in U.S. Pat. No. 5,340,716 (Ullman, et al.), the entire contents of which are hereby expressly incorporated herein by reference.

Any target analyte-specific binding partners known in the art or otherwise contemplated herein may be utilized in accordance with the present disclosure. Non-limiting examples of analyte-specific binding partners for target analytes include an antibody, a receptor, a ligand, an aptamer, a molecular imprinted polymer (i.e., inorganic matrix), and any combinations or derivatives thereof, as well as any other molecules capable of specific binding to the target analyte. In a particular (but non-limiting) example, each of the first and second analyte-specific binding partners of (a) and (b) is an antibody against the target analyte. Likewise, each of the first and second analyte-specific binding partners of (e) and (f), if present, may be an antibody against the second target analyte, in a particular (but non-limiting) embodiment.

Any biotin-specific binding partners known in the art or otherwise contemplated herein may be utilized in accordance with the present disclosure. In certain non-limiting embodiments, the biotin-specific binding partner is an antibody against biotin. In other non-limiting embodiments, the biotin-specific binding partner is avidin or an analog thereof.

Any avidin analogs known in the art or otherwise contemplated herein may be utilized in accordance with the present disclosure, so long as the avidin or avidin analog is: (1) capable of association with the sensitizer; (2) capable of binding to the biotinylated analyte-specific binding partner; and (3) capable of binding to biotin that may be present in a sample. Non-limiting examples of avidin analogs that can be utilized in accordance with the present disclosure include those disclosed in Kang et al. (*J Drug Target* (1995) 3:159-65), the entire contents of which are expressly incorporated herein by reference. Particular non-limiting examples of avidin analogs include avidin, streptavidin, traptavidin, neutral avidin, Neutralite avidin, Neutravidin, Lite-avidin, succinylated avidin, other forms of modified or genetically engineered) avidin, esters, salts, and/or derivatives of any of the above, and the like.

In certain non-limiting embodiments, the singlet oxygen-activatable chemiluminescent compound of (a) and/or (b) has a hapten directly or indirectly bound thereto.

Any fluorescent molecules known in the art that are capable of being excited by the activated chemiluminescent compound and emitting light at a particular, detectable wavelength can be utilized in accordance with the present disclosure as the fluorescent molecules of (a) and (b) (as well as (e), if present), so long as the signals produced by each fluorescent molecule is detectable from the signals produced by the other fluorescent molecules utilized. That is, the fluorescent molecule of (a) must emit light at a wavelength that is sufficiently different from the wavelength at which the fluorescent molecule of (b) emits light so that the two signals can be distinguished from one another when detected simultaneously. In a particular (but non-limiting) example, each fluorescent molecule utilized in accordance with the present disclosure is independently selected from the group consisting of terbium, uranium, samarium, europium, gadolinium, and dysprosium. For example (but not by way of limitation), with respect to the generation of two or three signals that can be distinguished from one another when detected simultaneously, terbium emits light at a wavelength of about 545 nm, uranium emits light at a wavelength of about 612 nm, and samarium emits light at a wavelength of about 645 nm.

The assay components/reagents of the compositions/kits/microfluidic devices/methods may be provided in any form that allows them to function in accordance with the present disclosure. For example but not by way of limitation, each of the reagents may be provided in liquid form and disposed in bulk and/or single aliquot form within the kit. Alternatively, in a particular (but non-limiting) embodiment, one or more of the reagents may be disposed in the kit in the form of a single aliquot lyophilized reagent. The use of dried reagents in microfluidics devices is described in detail in U.S. Pat. No. 9,244,085 (Samproni), the entire contents of which are hereby expressly incorporated herein by reference.

In addition to the assay components/reagents described in detail herein above, the kits may further contain other reagent(s) for conducting any of the particular assays described or otherwise contemplated herein. The nature of these additional reagent(s) will depend upon the particular assay format, and identification thereof is well within the skill of one of ordinary skill in the art; therefore, no further description thereof is deemed necessary. Also, the components/reagents present in the kits may each be in separate containers/compartments, or various components/reagents can be combined in one or more containers/compartments, depending on the cross-reactivity and stability of the components/reagents. In addition, the kit may include a microfluidics device in which the components/reagents are disposed.

The relative amounts of the various components/reagents in the kits can vary widely to provide for concentrations of the components/reagents that substantially optimize the reactions that need to occur during the assay methods and further to optimize substantially the sensitivity of an assay. Under appropriate circumstances, one or more of the components/reagents in the kit can be provided as a dry powder, such as a lyophilized powder, and the kit may further include excipient(s) for dissolution of the dried reagents; in this manner, a reagent solution having the appropriate concentrations for performing a method or assay in accordance with the present disclosure can be obtained from these components. Positive and/or negative controls may also be included with the kit. In addition, the kit can further include a set of written instructions explaining how to use the kit. A kit of this nature can be used in any of the methods described or otherwise contemplated herein.

Certain additional non-limiting embodiments of the present disclosure are directed to a microfluidics device that includes the components of any of the kits described herein above. In particular, certain non-limiting embodiments include a microfluidics device for determining the concentration of biotin and at least one additional target analyte in a sample. The microfluidics device comprises (i) an inlet channel through which a sample is applied; and (ii) at least a first compartment capable of being in fluidic communication with the inlet channel. The compartment(s) of (ii) contains: (a) at least a first composition comprising a singlet oxygen-activatable chemiluminescent compound and having biotin or an analog thereof directly or indirectly bound thereto, the first composition further comprising a fluorescent molecule that is excited by the activated chemiluminescent compound; (b) at least a second composition comprising a singlet oxygen-activatable chemiluminescent compound and having a first analyte-specific binding partner for a target analyte directly or indirectly bound thereto, the second composition further comprising a fluorescent molecule that is excited by the activated chemiluminescent compound, wherein the fluorescent molecule is different from the fluorescent molecule of (a) and emits light at a different wavelength than the fluorescent molecule of (a); (c) a biotinylated second analyte-specific binding partner for the target analyte, wherein the second analyte-specific binding partner binds to a different epitope of the target analyte than the first analyte-specific binding partner of (b); and (d) a composition comprising a sensitizer capable of generating singlet oxygen in its excited state and having a biotin-specific binding partner directly or indirectly bound thereto. In certain particular (but non-limiting) embodiments, the compartment(s) of (ii) further contains at least a third composition comprising a singlet oxygen-activatable chemiluminescent compound and having a second target analyte or an analog thereof directly or indirectly bound thereto, the second composition further comprising a fluorescent molecule that is excited by the activated chemiluminescent compound, wherein the fluorescent molecule is different from the fluorescent molecules of (a) and (b) and emits light at a different wavelength than the fluorescent molecules of (a) and (b).

Any of the singlet oxygen-activatable chemiluminescent compounds, sensitizers, fluorescent molecules, biotin or analogs thereof, target analytes or analogs thereof, and target analyte-specific binding partners described in detail herein above or otherwise contemplated herein may be utilized in the microfluidics devices of the present disclosure.

For example, in certain particular (but non-limiting) embodiments, the singlet oxygen-activatable chemiluminescent compounds of (a) and (b) are substances that undergo a chemical reaction with singlet oxygen to form a metastabile intermediate species that can decompose with the simultaneous or subsequent emission of light.

In particular (but non-limiting) embodiments, the sensitizer is a photosensitizer.

In particular (but non-limiting) embodiments, each of the first and second analyte-specific binding partners of (b) and (c) is an antibody against the target analyte.

In particular (but non-limiting) embodiments, the biotin-specific binding partner of (iii) is avidin or an analog thereof, or is an antibody against biotin.

In particular (but non-limiting) embodiments, the singlet oxygen-activatable chemiluminescent compound of (a) and/or (b) has a hapten directly or indirectly bound thereto.

In particular (but non-limiting) embodiments, the fluorescent molecules of (a) and (b) are each independently selected from the group consisting of terbium, uranium, samarium, europium, gadolinium, and dysprosium. For example (but not by way of limitation), terbium emits light at a wavelength of about 545 nm, uranium emits light at a wavelength of about 612 nm, and samarium emits light at a wavelength of about 645 nm.

In particular (but non-limiting) embodiments, the compartment(s) of (ii) further contains: (e) at least a third composition comprising a singlet oxygen-activatable chemiluminescent compound and having a first analyte-specific binding partner for a second target analyte directly or indirectly bound thereto, the second composition further comprising a fluorescent molecule that is excited by the activated chemiluminescent compound, wherein the fluorescent molecule is different from the fluorescent molecules of (a) and (b) and emits light at a different wavelength than the fluorescent molecules of (a) and (b); and (f) a biotinylated second analyte-specific binding partner for the second target analyte, wherein the second analyte-specific binding partner binds to a different epitope of the second target analyte than the first analyte-specific binding partner of (e). In a particular (but non-limiting) embodiment, the fluorescent molecule of the third composition is selected from the group consisting of terbium, uranium, samarium, europium, gadolinium, and dysprosium.

In certain non-limiting embodiments, all of elements (a)-(d) (and (e) and (f), when present) of (ii) are present in the same compartment. In alternative non-limiting embodiments, elements (a)-(d) (and (e) and (f), when present) are split between two or more compartments.

The device may be provided with any arrangement of the compartments and distribution of the various components therebetween that allows the device to function in accordance with the present disclosure.

Any of the compartments of the microfluidics device may be sealed to maintain reagent(s) disposed therein in a substantially air tight environment until use thereof; for example, compartments containing lyophilized reagent(s) may be sealed to prevent any unintentional reconstitution of the reagent. The inlet channel and a compartment, as well as two compartments, may be described as being "capable of being in fluidic communication" with one another; this phrase indicates that each of the compartment(s) may still be sealed, but that the two compartments are capable of having fluid flow therebetween upon puncture of a seal formed therein or therebetween.

The microfluidics devices of the present disclosure may be provided with any other desired features known in the art or otherwise contemplated herein. For example but not by way of limitation, the microfluidics devices of the present disclosure may further include a read chamber; the read chamber may be any of the compartments containing the reagents described herein above, or the read chamber may be in fluidic communication with said compartment. The microfluidics device may further include one or more additional compartments containing other solutions, such as (but not limited to) wash solutions, dilution solutions, excipients, interference solutions, positive controls, negative controls, quality controls, and the like. These additional compartment(s) may be in fluidic communication with one or more of the other compartments. For example, the microfluidics device may further include one or more compartments containing a wash solution, and these compartment(s) may be capable of being in fluidic communication with any other compartment(s) of the device. In another example, the microfluidics device may further include one or more compartments containing an excipient for dissolution of one or more dried reagents, and the compartment(s) may be capable of being in fluidic communication with any other compartment(s) of the device. In yet a further example, the microfluidics device may include one or more compartments containing a dilution solution, and the compartment(s) may be capable of being in fluidic communication with any other compartment(s) of the device.

In addition, any of the kits/microfluidics devices described or otherwise contemplated herein may include more than one target analyte assay multiplexed with the biotin assay in a single kit/device. When multiple target analyte assays are present, each of the assays may be constructed and function as described herein. Alternatively, the biotin and target analyte assays described herein may be multiplexed with any other target analyte assay known in the art that is capable of being contained within the kits/microfluidics devices of the present disclosure. Non-limiting examples of other assays that may be multiplexed with the assays disclosed and claimed herein include BNP, NT-proBNP, D-Dimer, CKMB, Myoglobin, Myeloperoxidase, ST2, PCT, hCG, LH, FSH, iPTH, TSH, $fT_4$, $T_4$, PSA, fPSA, and cPSA, and combinations thereof.

When multiple target analyte assays are present in a single microfluidics device, multiple inlet channels may be connected to the sample application chamber. In certain embodiments, a portion of the sample may be passed from the sample application chamber to the multiple inlet channels without regard for the content thereof. Alternatively, structure(s) may be present in the sample application chamber, the inlet channels, and/or the connection therebetween that allow for separation of certain components from the whole sample and delivery of said components to the different assays. A non-limiting example of a sample distribution device that may be utilized in accordance with the present disclosure is described in detail in U.S. Pat. No. 9,416,776 (Ledden, et al.), the entire contents of which are hereby expressly incorporated herein by reference.

Certain non-limiting embodiments are also directed to a method for detecting the presence and/or concentration of biotin and at least one additional target analyte in a sample. The method comprises the following steps.

In the first step, a sample suspected of containing biotin and at least one additional target analyte is combined, either simultaneously or wholly or partially sequentially, with: (a) at least a first composition comprising a singlet oxygen-activatable chemiluminescent compound and having biotin or an analog thereof directly or indirectly bound thereto, the first composition further comprising a fluorescent molecule that is excited by the activated chemiluminescent compound; (b) at least a second composition comprising a singlet oxygen-activatable chemiluminescent compound and having a first analyte-specific binding partner of a target analyte directly or indirectly bound thereto, the second composition further comprising a fluorescent molecule that is excited by the activated chemiluminescent compound, wherein the fluorescent molecule is different from the fluorescent molecule of (a) and emits light at a different wavelength than the fluorescent molecule of (a); (c) a biotinylated second analyte-specific binding partner for the target analyte, wherein the second analyte-specific binding partner binds to a different epitope of the target analyte than the first analyte-specific binding partner of (b); and (d) an excess of a composition comprising a sensitizer capable of generating singlet oxygen in its excited state and having a biotin-specific binding partner directly or indirectly bound thereto.

In the second step, the components are incubated together to allow for the binding of (b) and (c) to target analyte present in the sample as well as the binding of (c) to (d), wherein the indirect binding of (b) to (d) (via (c) and target analyte) results in the formation of a target analyte complex in which the sensitizer is brought into close proximity to the chemiluminescent compound. In addition, (a) binds to (d) in the absence of biotin in the sample and results in the formation of a biotin complex in which the sensitizer is brought into close proximity to the chemiluminescent compound.

In the third step, the sensitizer is activated to generate singlet oxygen, wherein activation of the sensitizers present in the biotin complex and in the target analyte complex causes the activation of the chemiluminescent compound present in each complex.

In the fourth step, the amount of chemiluminescence generated by the activated chemiluminescent compound in the biotin complex is determined by measuring the amount of light emitted by the fluorescent molecule of (a), wherein the amount of biotin in the sample is inversely proportional to the amount of light emitted.

In the fifth step, the amount of chemiluminescence generated by the activated chemiluminescent compound in the target analyte complex is determined by measuring the amount of light emitted by the fluorescent molecule of (b) to determine the amount of target analyte in the sample.

In the sixth step, the second-fifth steps can be optionally repeated, if desired.

In the seventh step, the result of step (5) is corrected based upon any biotin interference detected in step (4). Alternatively, the result of step (5) is flagged as unreliable if the biotin concentration detected in step (4) is above a maximum threshold level.

In certain non-limiting embodiments of the method, step (1) further comprises combining with elements (a)-(d): (e) at least a third composition comprising a singlet oxygen-activatable chemiluminescent compound having a first analyte-specific binding partner for a second target analyte directly or indirectly bound thereto, the third composition further comprising a fluorescent molecule that is excited by the activated chemiluminescent compound, wherein the fluorescent molecule is different from the fluorescent molecules of (a) and (b) and emits light at a different wavelength than the fluorescent molecules of (a) and (b); and (f) a biotinylated second analyte-specific binding partner for the second target analyte, wherein the second analyte-specific binding partner binds to a different epitope of the second target analyte than the first analyte-specific binding partner of (e). In this instance, the method may further comprise the steps of: (8) determining the amount of chemiluminescence generated by the activated chemiluminescent compound in the second target analyte complex by measuring the amount of light emitted by the fluorescent molecule of (e) to determine the amount of target analyte in the sample; and (9) correcting the result of step (8) based upon any biotin interference detected in step (4) and/or flagging the result of step (8) as being unreliable if the biotin concentration detected in step (4) is above a maximum threshold level.

Any of the singlet oxygen-activatable chemiluminescent compounds, sensitizers, fluorescent molecules, biotin or analogs thereof, target analytes or analogs thereof, and target analyte-specific binding partners described in detail herein above or otherwise contemplated herein may be utilized in the methods of the present disclosure.

For example, in certain particular (but non-limiting) embodiments, the singlet oxygen-activatable chemiluminescent compounds of (a) and (b) (and (e), when present) are substances that undergo a chemical reaction with singlet oxygen to form a metastabile intermediate species that can decompose with the simultaneous or subsequent emission of light.

In particular (but non-limiting) embodiments, the sensitizer is a photosensitizer, and the activation of the sensitizer in step (3) comprises irradiation with light (such as, but not limited to, irradiation at about 680 nm).

In particular (but non-limiting) embodiments, each of the first and second analyte-specific binding partners of (b) and (c) (as well as (e) and (f), if present) is an antibody against the target analyte.

In particular (but non-limiting) embodiments, the biotin-specific binding partner of (d) is avidin or an analog thereof, or is an antibody against biotin.

In particular (but non-limiting) embodiments, the singlet oxygen-activatable chemiluminescent compound of (a) and/or (b) has a hapten directly or indirectly bound thereto.

In particular (but non-limiting) embodiments, the fluorescent molecules of (a) and (b) (and (e), if present) are each independently selected from the group consisting of terbium, uranium, samarium, europium, gadolinium, and dysprosium. For example (but not by way of limitation), terbium emits light at a wavelength of about 545 nm, uranium emits light at a wavelength of about 612 nm, and samarium emits light at a wavelength of about 645 nm.

Any sample for which an assay for the presence of biotin is desired can be utilized as the sample in accordance with the methods of the present disclosure. Non-limiting examples of samples include a biological sample such as, but not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof. Particular non-limiting examples include lysed whole blood cells and lysed red blood cells.

As mentioned above, the various components of the method are provided in combination (either simultaneously or sequentially). When the various components of the method are added sequentially, the order of addition of the components may be varied; a person having ordinary skill in the art can determine the particular desired order of addition of the different components to the assay. The simplest order of addition, of course, is to add all the materials simultaneously and determine the signals produced therefrom. Alternatively, each of the components, or groups of components, can be combined sequentially. In certain embodiments, an incubation step may be involved subsequent to one or more additions.

In an alternative (but non-limiting) embodiment, step (1) of the method includes first combining the sample with the biotinylated target analyte-specific binding partner and the composition comprising the sensitizer and incubating same before adding the compositions comprising the singlet oxygen-activatable chemiluminescent compounds. Alternatively, step (1) of the method can include first combining the sample with the compositions comprising the singlet oxygen-activatable chemiluminescent compounds and incubating same before adding the composition comprising the sensitizer. In this latter embodiment, the biotinylated target analyte-specific binding partner may be added before or after the incubation step.

While particular embodiments of the present disclosure are described as having the LOCI® assay format, it is to be understood that the present disclosure is also directed to other assay formats (and kits, microfluidics devices, and methods of performing same) for which elimination of sample biotin interference is desired. For example (but not by way of limitation), the present disclosure also includes assay formats where different signal molecules such as (but not limited to) different antibodies linked to different enzymes that generate signals at different wavelengths can be utilized in place of the chemiluminescent compound-containing compositions described herein above.

EXAMPLES

Examples are provided hereinbelow. However, the present disclosure is to be understood to not be limited in its application to the specific experimentation, results, and laboratory procedures disclosed herein. Rather, the Examples are simply provided as one of various embodiments and are meant to be exemplary, not exhaustive.

Example 1

FIG. 1 depicts the assay components present in the kits and microfluidic devices and used in the methods of certain non-limiting embodiments of the present disclosure. These components include (from left to right):
(i) a first chemibead having biotin or an analog thereof directly or indirectly bound thereto and containing a first fluorescent molecule that is excited by activated chemiluminescent compound present in the chemibead;
(ii) a sensibead capable of generating singlet oxygen in its excited state and having a biotin-specific binding partner directly or indirectly bound thereto;
(iii) a biotinylated target analyte-specific binding partner; and
(iv) a second chemibead having target analyte or an analog thereof directly or indirectly bound thereto and containing a second fluorescent molecule that is excited by activated chemiluminescent compound present in the chemibead.

The first and second fluorescent molecules are different from one another and emit light at different wavelengths; in this manner, assays for both biotin and target analyte can be performed simultaneously in the same reaction, as complexes containing (i) are detected at a different wavelength from complexes containing (iv).

Figure 2:
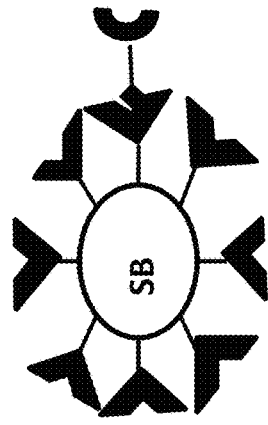
FIG. 2 schematically depicts complexes formed from the multiplex assay components of FIG. 1, depending on whether or not biotin and a target analyte are present in a test sample.
Figure 2:
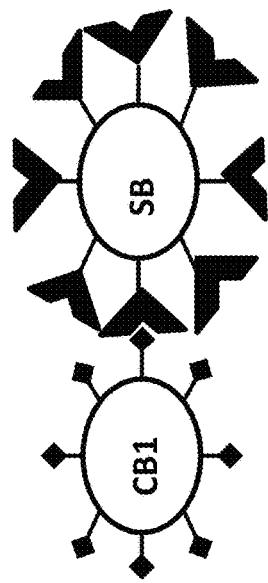
Figure 2:
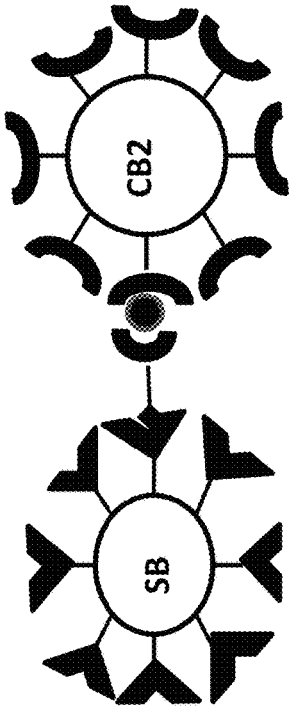
Figure 2:
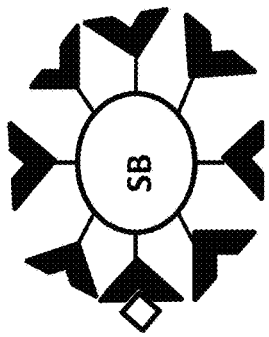

When biotin is not present in the sample, a complex is formed between (i) and (ii), as shown on the left side of the upper panel of FIG. 2, and a signal is generated upon activation of the sensitizer. However, when biotin is present in the sample, it competes with (i) for binding to (ii), as shown in the left side of the lower panel of FIG. 2. Thus, the presence of biotin in the sample is detected as a decrease in the signal detected at the first wavelength used to detect light emitted from the first fluorescent molecule.

In addition, in the same reaction, (iii) binds to target analyte present in the sample, and then (iv) binds to (iii), as shown on the right side of the lower panel of FIG. 2. As such, the presence of target analyte in the sample is detected as an increase in the signal detected at the second wavelength used to detect light emitted from the second fluorescent molecule. In contrast, when no target analyte is present, only (iii) can bind to (ii), but (iv) is not capable of binding thereto, and thus a signal is not generated in the absence of target analyte (left side of upper panel of FIG. 2).

If biotin is detected in the sample, then the result obtained from the target analyte assay con be corrected based upon any biotin interference detected using the first chemibead and/or flagged as unreliable if the detected biotin concentration is above a maximum threshold level.

Further, the multiplex assays of the present disclosure can be adapted to simultaneously detect more than one target analyte in addition to the detection of biotin interference. For each additional target analyte to be detected, additional components like (iii) and (iv) are added, wherein the fluorescent molecule present in the additional component like (iv) differs from the first and second fluorescent molecules in that it emits light at a different and separately detectable wavelength than the first and second fluorescent molecules. In this manner, two, three, four, five, six, seven, eight, nine, ten, or more target analytes can be detected in a single reaction, so long as the chemibeads used to detect each contain different fluorescent molecules that each emit light at different and separately detectable wavelengths; as such, the limiting factor in how many target analytes can be detected in a single reaction are the number of fluorescent molecules available that function as described herein.

Example 2

Figure 3:
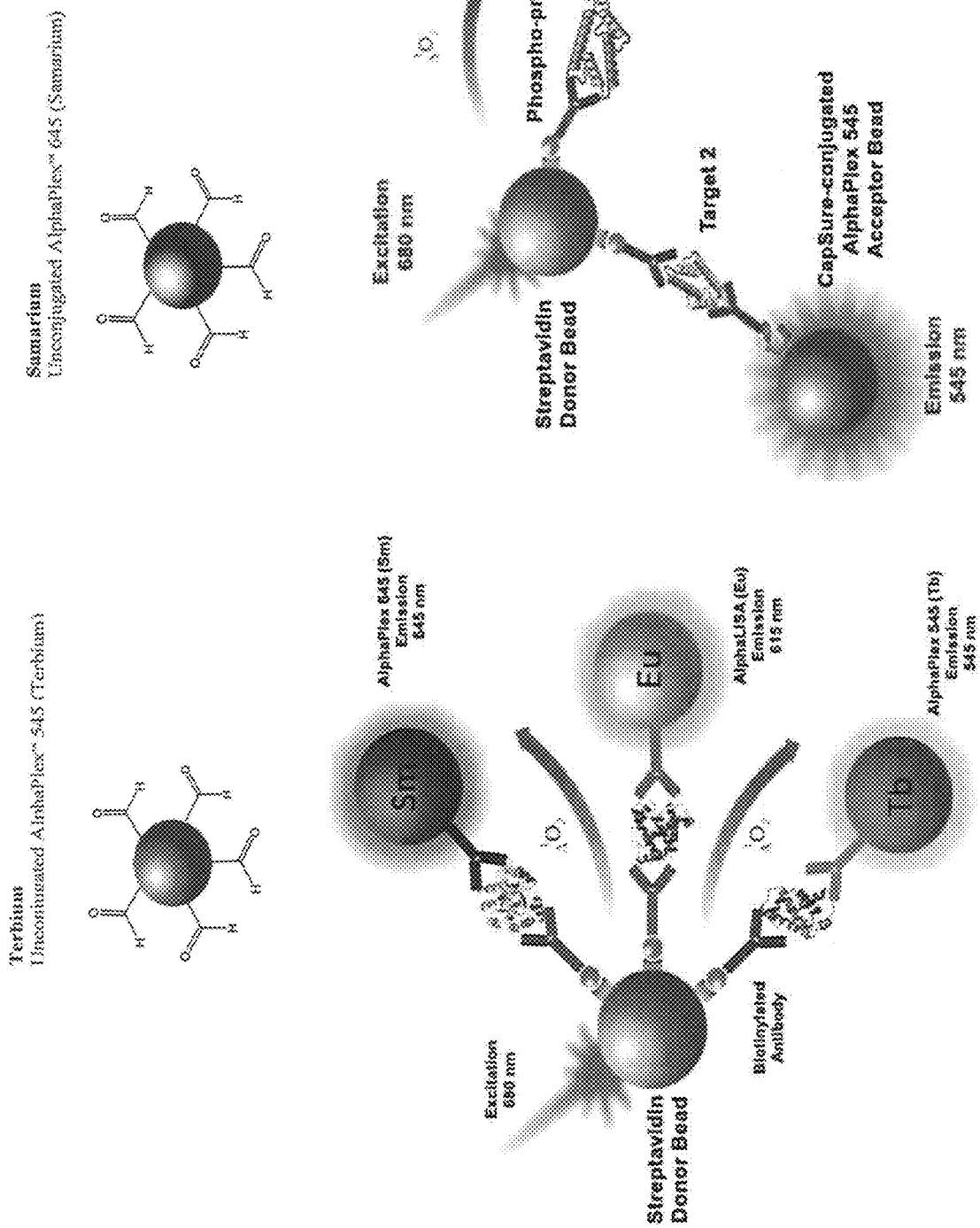
FIG. 3 schematically depicts two non-limiting embodiments of acceptor beads that can be utilized in accordance with the present disclosure (upper panel), and a multiplex assay performed in accordance with the present disclosure (lower panel).

This Example provides a multiplexed assay for biotin and procalcitonin (PCT). Biotin is covalently conjugated to chemibeads dyed with terbium (FIG. 3, left side of upper panel), and capture antibody for PCT is covalently conjugated to chemibeads dyed with europium (FIG. 3, right side of upper panel). The multiplexed method is calibrated with a multi-analyte calibrator containing at least both biotin and PCT. The same streptavidin sensibeads are used for detecting both biotin and PCT.

As shown in the lower panel of FIG. 3, the sensibeads are activated by excitation light at 680 nm to generate singlet oxygen, and singlet oxygen diffuses into both types of chemibeads. When complexed with biotin, the biotin chemibeads emit light at 545 nm, which is measured as a biotin signal. When complexed with PCT, the PCT chemibead emit light at 612 nm, which is measured as a PCT signal. Two calibration curves are then generated from the multiplex measurements: one for biotin and one for PCT.

The measured biotin concentration in a sample using terbium as the fluorescent molecule is related to the biotin LOCI® signal measured using europium as the fluorescent molecule. The LOCI® signal at varying biotin concentrations measured by europium is experimentally obtained. The biotin LOCI® signal by europium at certain biotin concentration can then be predicted (extrapolated) and, if necessary, subsequently subtracted (if a positive impact on signal is observed) or added (if a negative impact on signal is observed) to correct the results of the target analyte.

In this manner, the target analyte assay results can be corrected using the biotin signal deduced from the biotin measurement in multiplex fashion. Alternatively, the result can be flagged as unreliable if the detected biotin concentration is above a maximum threshold level.

Example 3

Figure 4:
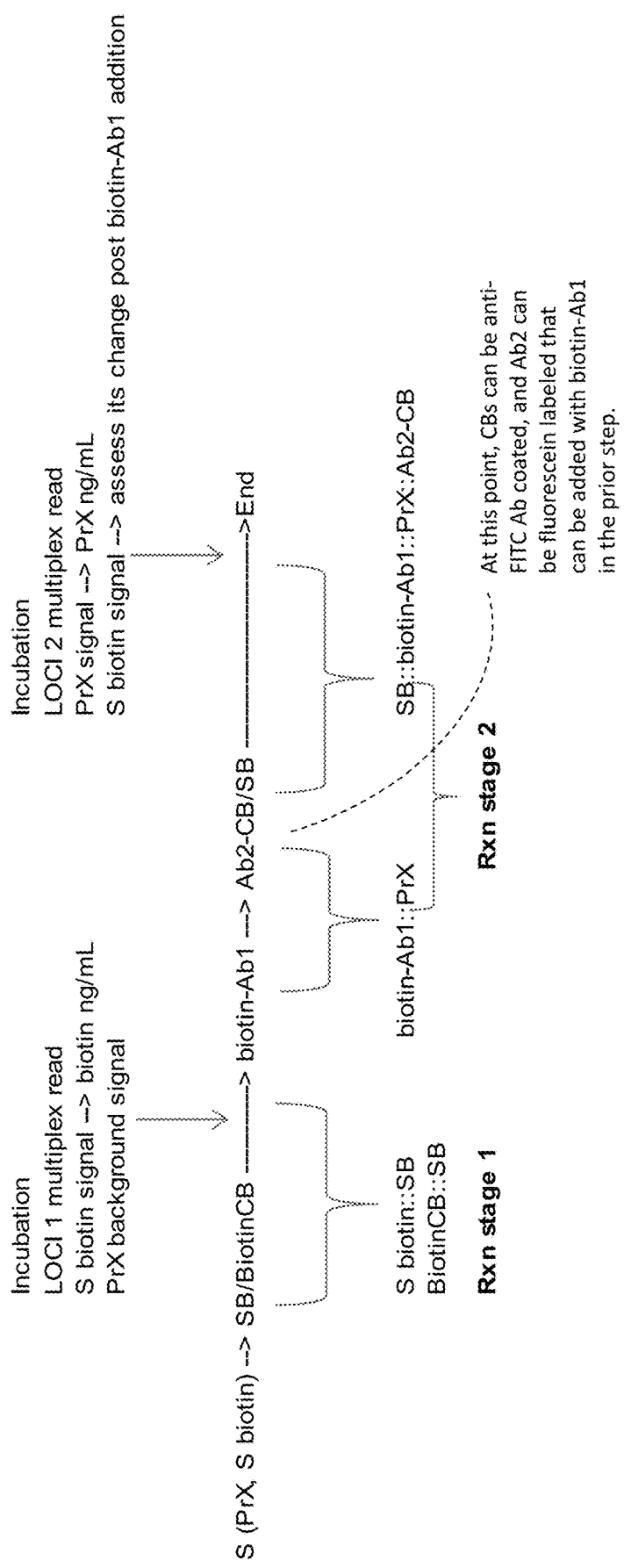
FIG. 4 depicts an assay sequence for one non-limiting embodiment of the multiplex assay constructed in accordance with the present disclosure, in which two analytes, Protein X (PrX) and biotin are to be measured. S, sample. S biotin, sample biotin. Ab1, first antibody to PrX. Ab2, second antibody to PrX. CB, chemibead. SB, sensibead. "::" represents binding.

FIG. 4 depicts an assay sequence for one non-limiting embodiment of the multiplex assay constructed in accordance with the present disclosure, in which two analytes are to be measured: the target analyte (referred to in this Example as Protein X (PrX)) and biotin. The assay for the target analyte PrX is a sandwich assay that requires the use of two antibodies; the first antibody (Ab1) is coated on chemibeads (Ab1-CBs), and the second antibody (Ab2) is biotinylated. The biotin assay uses a competitive format and requires the use of biotin- (or biotin analog-) coated chemibeads (Biotin-CBs). Ab1-CBs and Biotin-CBs each contain a different dye, so that complexes containing the two chemibeads can be separately detected in a single reaction. In addition, both assays use the same streptavidin-coated sensibeads (SBs).

While FIG. 4 depicts one addition sequence for this multiplex assay, such sequence is not to be considered limiting to the present disclosure; indeed, the various assay components may be added in any order, and the two assays may be performed in any desired sequence. Thus, the order of addition and sequence of assays shown in FIG. 4 is non-limiting to the scope of the present disclosure.

Figure 5:
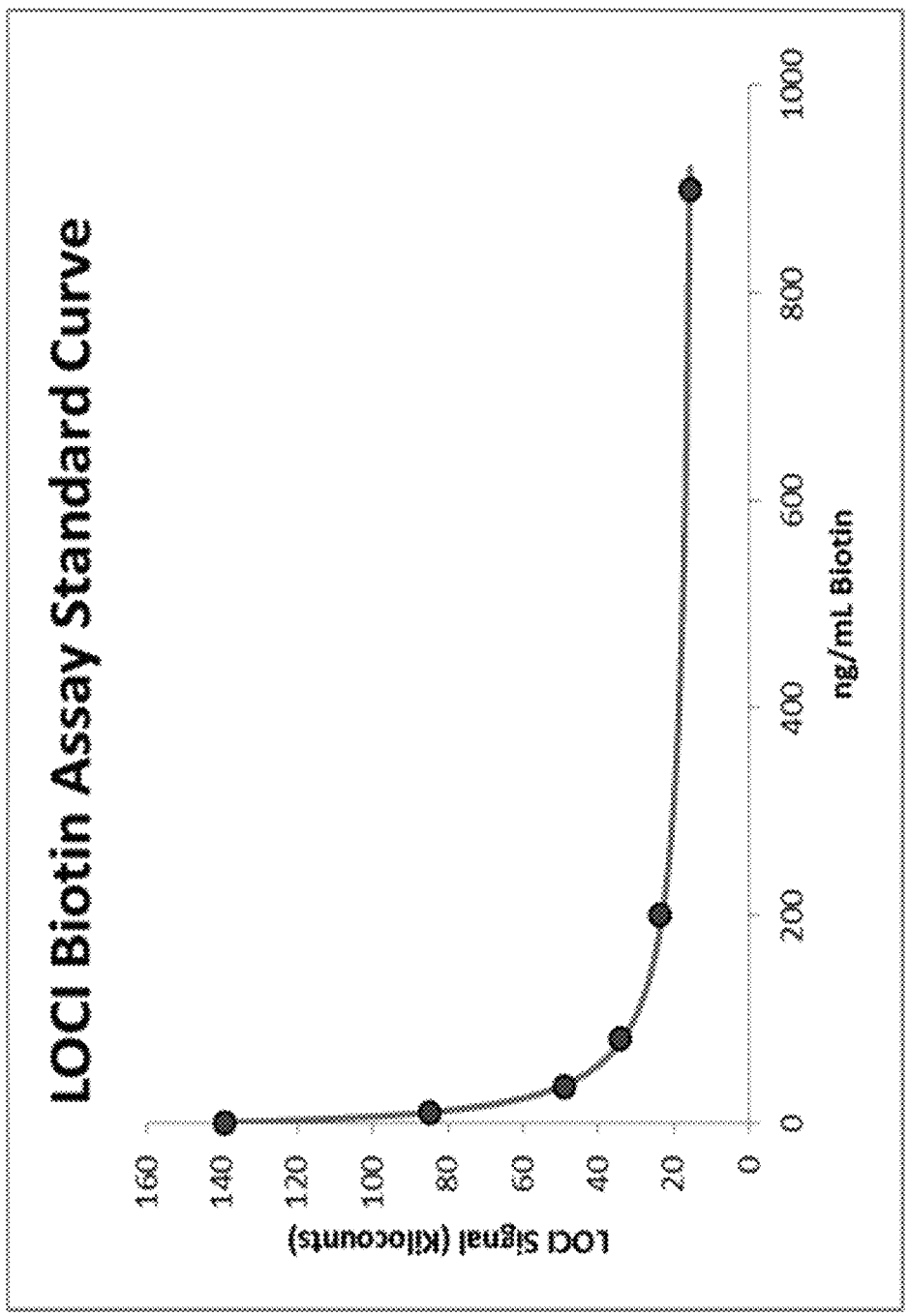
FIG. 5 graphically depicts how biotin signal can be translated into a concentration ([biotin] ng/ml) by proper calibration.

A biotin signal obtained from the biotin assay described above can be translated into a sample biotin concentration ([biotin] ng/ml) by proper calibration utilizing a standard curve, as shown in FIG. 5 (and described in detail in U.S. Ser. No. 62/711,694 (filed Jul. 30, 2018). In certain non-limiting embodiments, this concentration may be obtained prior to assaying for the target analyte. The calculated biotin concentration may be utilized in one of four different ways:

(1) If the biotin signal or calculated biotin concentration is below a threshold above which it is known that biotin starts interfering with the target analyte assay, then report the target analyte assay result as normal.

(2) If the biotin signal or calculated biotin concentration is above a threshold level (i.e., above the level at which it is known that biotin starts interfering with the target analyte assay), then the target analyte result is flagged as unreliable and is not reported.

(3) If the biotin signal or calculated biotin concentration is above the threshold level, utilize the biotin concentration or signal value to correct the target analyte assay result.

(4) This option utilizes a combination of (1), (2), and (3)—i.e., correct the affected target analyte assay result when the biotin level is above the threshold level for affecting the target analyte assay but not overwhelmingly exceeding the threshold level. If the biotin signal/calculated concentration detected is low (i.e., below a threshold level, such that biotin does not interfere with the target analyte results), the target analyte result is reported as normal. If the biotin signal/calculated concentration detected is too high (i.e., above a maximum threshold level) and correction is not possible, then a flag should be tripped, and the target analyte result flagged as unreliable.

Figure 6:
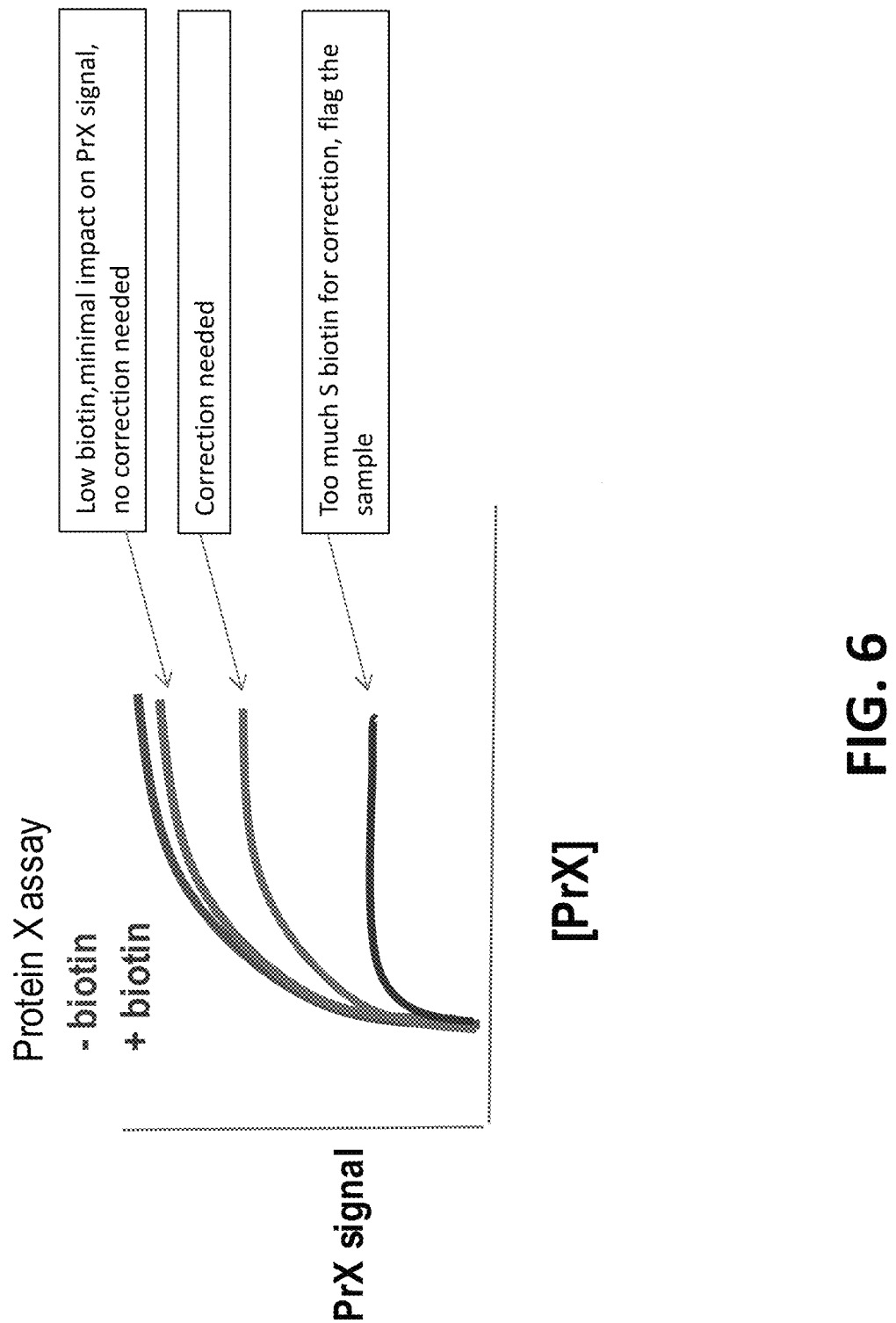
FIG. 6 graphically depicts various scenarios related to biotin interference with a target analyte signal and the correction thereof in one non-limiting embodiment of the multiplex assay according to the present disclosure.

FIG. 6 graphically depicts these various scenarios related to biotin interference with a target analyte signal and the possible correction thereof. The uppermost curve indicates the assay values obtained when no biotin is present. In the curve immediately below the uppermost curve, a low biotin concentration is present that has a minimal impact on the target analyte signal; in this scenario, no correction of the target analyte result is needed. In the next curve, the biotin concentration/signal exceeds a threshold value above which biotin interferes with the target analyte assay; in this scenario, correction of the target analyte result based upon the amount of biotin interference detected is required. That is, the biotin concentration or signal value is utilized to correct the target analyte assay result. In the lowest curve, the biotin concentration or signal value is significantly above the threshold value and exceeds a maximum threshold value above which the target analyte concentration can no longer be corrected; thus, the amount of biotin interference present causes a flag to be tripped to indicate that the target analyte result is unreliable.

With respect to the components of the assay, when there is no or minimal biotin present in the sample, all biotin-chemibeads are bound to sensibeads in "Rxn stage 1" of FIG. 4; in this instance, there is no biotin interference of the target analyte signal. When sample biotin is sufficiently high, some of the sample biotin and biotin-chemibeads are not bound to sensibeads added in "Rxn stage 1" of FIG. 4, and thus carry over to the sensibead binding reaction in "Rxn stage 2" of FIG. 4. A sufficient amount of sample biotin and biotin-chemibead spill-over will affect the formation of the sensibead/biotin-antibody 1/target analyte/antibody 2-chemibead complex (depicted in FIG. 4 as "SB::biotin-Ab1::PrX::Ab2-CB") in "Rxn stage 2" of FIG. 4, thus resulting in reduced target analyte signal, as shown in the graph of FIG. 6.

The upper table in FIG. 7 depicts a hypothetical scenario of target analyte (PrX) signal (in kilocounts) obtained by the multiplex assay according to the present disclosure in the absence and presence of sample biotin. As can be seen, at the arbitrary minimum sample biotin concentration (10 ng/ml), no effect on target analyte signal is observed at any of the target analyte concentrations tested. Once a threshold biotin concentration is passed (such as at the arbitrary values of 100 ng/ml and 500 ng/ml), the effect of sample biotin concentration on the PrX signal can be observed, and the PrX value can subsequently be corrected based on the amount of biotin interference present. However, once a maximum threshold level is reached (such as the arbitrary value of 3000 ng/ml), the effect of biotin interference on PrX signal is so great that it is no longer possible to correct for biotin interference, and thus the PrX signal must be flagged as unreliable. Please note that the disclosure of the arbitrary value of 3000 ng/ml is solely for illustrative purposes only; the scope of the present disclosure includes any threshold values calculated as described or otherwise contemplated herein, and includes threshold values much lower than 3000 ng/ml as well as threshold values much higher than 3000 ng/ml While the upper table of FIG. 7 depicts the actual target analyte signal detected, the lower table of FIG. 7 depicts the percent interference by sample biotin on PrX signal (based on the values in the upper table). As can be seen, a different percentage of interference is seen at different PrX concentrations, even when the sample biotin concentration remains constant.

FIGS. 8 and 9 illustrate two methods by which the target analyte signal can be corrected based upon the sample biotin signal/concentration detected. The method illustrated in FIG. 9 utilizes all of the data present in FIG. 7, whereas the method illustrated in FIG. 8 utilizes a subset of the data from FIG. 7. However, it is to be understood that these two examples are provided for purposes of illustration, and any methods by which the target analyte signal can be corrected based upon sample biotin signal/concentration that will be apparent to a person having ordinary skill in the art may be utilized in accordance with the present disclosure.

In FIG. 8, the shaded rectangle in the upper table (which is simply reproduced from FIG. 7) is utilized to correct the PrX signal using the sample biotin signal/concentration to provide a more localized correction of the PrX signal. As shown in the lower table of FIG. 8, the values from the shaded rectangle are rearranged and then entered into statistical software that conducts a regression to obtain a correction equation based on the data from the shaded rectangle. The regression correction equation obtained in this example is shown at the bottom of FIG. 8.

This step can be completed during co-calibration (either in manufacturing or by customer calibration) with calibrators containing both PrX and biotin at varying known concentrations. The two-analyte co-calibration creates a surface equation separate from the calibrations for each of biotin and PrX. The biotin or PrX single analyte calibration is done in the absence of the other analyte. But this co-calibration is performed when both analytes are present at varying concentrations. The purpose of the co-calibration is to obtain a surface equation where PrX concentration (or PrX signal at 0 ng/ml biotin) serves as a function of PrX signal in the presence of biotin interference).

The reason for using subsets of data in the method of FIG. 8 is to ensure more accurate regression for correction at a more local level. So if the PrX signal and biotin signal/ concentration (ng/ml) are known, then an accurate PrX concentration (ng/ml) can be calculated.

Alternatively, the corrected PrX concentration can be caluculated by performing a similar regression that utilizes the entire table or the entire assay ranges (biotin and PrX) obtained, as shown in FIG. 9. On the left side of FIG. 9, the data from FIG. 7 has simply been rearranged into the table shown. Then a regression analysis is performed as described herein above to obtain a regression equation, as shown on the right side of FIG. 9.

Regardless of which particular method is used, the methods of FIGS. 8 and 9 both produce regression equations to predict target analyte (PrX) concentration in the presence of biotin interference.

Thus, in accordance with the present disclosure, there have been provided compositions, kits, and devices, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A method for detecting the presence and/or concentration of biotin and an at least one target analyte in a sample, the method comprising the steps of:
    (1) combining, either simultaneously or wholly or partially sequentially, a sample suspected of containing biotin and at least one additional target analyte with:
        (a) at least a first composition comprising a singlet oxygen-activatable chemiluminescent compound and having biotin or an analog thereof directly or indirectly bound thereto, the first composition further comprising a fluorescent molecule that is excited by the activated chemiluminescent compound;
        (b) at least a second composition comprising a singlet oxygen-activatable chemiluminescent compound and having a first analyte-specific binding partner of a target analyte directly or indirectly bound thereto, the second composition further comprising a fluorescent molecule that is excited by the activated chemiluminescent compound, wherein the fluorescent molecule is different from the fluorescent molecule of (a) and emits light at a different wavelength than the fluorescent molecule of (a);
        (c) a biotinylated second analyte-specific binding partner for the target analyte, wherein the second analyte-specific binding partner binds to a different epitope of the target analyte than the first analyte-specific binding partner of (b); and
        (d) a composition comprising a sensitizer capable of generating singlet oxygen in its excited state and having a biotin-specific binding partner directly or indirectly bound thereto;
    (2) allowing the binding of (b) and (c) to target analyte present in the sample as well as the binding of (c) to (d), wherein the indirect binding of (b) to (d) via (c) and target analyte results in the formation of a target analyte complex in which the sensitizer is brought into close proximity to the chemiluminescent compound, and wherein (a) binds to (d) in the absence of biotin in the sample and results in the formation of a biotin complex in which the sensitizer is brought into close proximity to the chemiluminescent compound, and (3) activating the sensitizer to generate singlet oxygen, wherein activation of the sensitizers present in the biotin complex and in the target analyte complex causes the activation of the chemiluminescent compound present in each complex;

(4) determining the amount of chemiluminescence generated by the activated chemiluminescent compound in the biotin complex by measuring the amount of light emitted by the fluorescent molecule of (a), wherein the amount of biotin in the sample is inversely proportional to the amount of light emitted;

(5) determining the amount of chemiluminescence generated by the activated chemiluminescent compound in the target analyte complex by measuring the amount of light emitted by the fluorescent molecule of (b) to determine the amount of target analyte in the sample;

(6) optionally repeating steps (2)-(5); and (7) correcting the result of step (5) based upon the amount of biotin in the sample detected in step (4) or flagging the result of step (5) as being unreliable if the biotin concentration detected in step (4) is above a maximum threshold level.

2. The method of claim 1, wherein the singlet oxygen-activatable chemiluminescent compound is a substance that undergoes a chemical reaction with singlet oxygen to form a metastabile intermediate species that can decompose with the simultaneous or subsequent emission of light.

3. The method of claim 1, wherein the sensitizer is a photosensitizer, and the activation of the sensitizer in step (3) comprises irradiation with light.

4. The method of claim 1, wherein the sample is a biological sample.

5. The method of claim 4, wherein the biological sample is selected from the group consisting of whole blood or any portion thereof, urine, saliva, sputum, cerebrospinal fluid, skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

6. The method of claim 1, wherein each of the first and second analyte-specific binding partners of (b) and (c) is an antibody against the target analyte.

7. The method of claim 1, wherein the biotin-specific binding partner of (d) is avidin or an analog thereof.

8. The method of claim 1, wherein the biotin-specific binding partner of (d) is an antibody against biotin.

9. The method of claim 1, wherein the singlet oxygen-activatable chemiluminescent compound of (a) and/or (b) has a hapten directly or indirectly bound thereto.

10. The method of claim 1, wherein the fluorescent molecules of (a) and (b) are each independently selected from the group consisting of terbium, uranium, samarium, europium, gadolinium, and dysprosium.

11. The method of claim 10, wherein:
terbium emits light at a wavelength of about 545 nm;
uranium emits light at a wavelength of about 612 nm; and
samarium emits light at a wavelength of about 645 nm.

12. The method of claim 1, wherein step (1) further comprises combining with (a)-(d):

(e) at least a third composition comprising a singlet oxygen-activatable chemiluminescent compound having a first analyte-specific binding partner for a second target analyte directly or indirectly bound thereto, the composition further comprising a fluorescent molecule that is excited by the activated chemiluminescent compound, wherein the fluorescent molecule is different from the fluorescent molecules of (a) and (b) and emits light at a different wavelength than the fluorescent molecules of (a) and (b); and (f) a biotinylated second analyte-specific binding partner for the second target analyte, wherein the second analyte-specific binding partner binds to a different epitope of the second target analyte than the first analyte-specific binding partner of (e).

13. The method of claim 12, wherein the method further comprises the steps of:

(8) determining the amount of chemiluminescence generated by the activated chemiluminescent compound in the second target analyte complex by measuring the amount of light emitted by the fluorescent molecule of (e) to determine the amount of target analyte in the sample; and (9) correcting the result of step (8) based upon the amount of biotin in the sample detected in step (4) or flagging the result of step (8) as being unreliable if the biotin concentration detected in step (4) is above a maximum threshold level.

14. The method of claim 12, wherein the fluorescent molecule of (e) is selected from the group consisting of terbium, uranium, samarium, europium, gadolinium, and dysprosium.

* * * * *